United States Patent
Kucek et al.

(10) Patent No.: US 6,832,199 B1
(45) Date of Patent: Dec. 14, 2004

(54) METHOD AND APPARATUS FOR RETRIEVING SERVICE TASK LISTS FROM REMOTELY LOCATED MEDICAL DIAGNOSTIC SYSTEMS AND INPUTTING SUCH DATA INTO SPECIFIC LOCATIONS ON A TABLE

(75) Inventors: Leo Michael Kucek, Waukesha, WI (US); Thomas L. Lamoureux, Waukesha, WI (US); Karamjeet Singh, Germantown, WI (US)

(73) Assignee: GE Medical Technology Services, Inc., Waukesha, WI (US)

(*) Notice: Subject to any disclaimer, the term of this patent is extended or adjusted under 35 U.S.C. 154(b) by 0 days.

(21) Appl. No.: 09/449,807

(22) Filed: Nov. 26, 1999

Related U.S. Application Data

(63) Continuation-in-part of application No. 09/199,685, filed on Nov. 25, 1998, now Pat. No. 6,353,445.

(51) Int. Cl.$^7$ .............................................. G06F 17/60
(52) U.S. Cl. ......................... 705/2; 600/300; 709/219; 705/9
(58) Field of Search .................. 705/2–4, 5–6, 705/7–9; 600/300–301, 437; 345/733, 961, 963; 700/65; 128/920; 709/203, 206, 318, 219; 702/183, 184; 399/9, 11

(56) References Cited

U.S. PATENT DOCUMENTS

| | | | |
|---|---|---|---|
| 5,077,666 A | * 12/1991 | Brimm et al. .................. 705/2 |
| 5,111,391 A | * 5/1992 | Fields et al. .................... 705/9 |
| 5,144,555 A | * 9/1992 | Takadachi et al. ........... 715/530 |
| 5,365,310 A | * 11/1994 | Jenkins et al. ................. 399/8 |
| 5,392,095 A | * 2/1995 | Siegel ............................ 399/8 |
| 5,482,050 A | * 1/1996 | Smokoff et al. ............ 600/523 |
| 5,594,840 A | * 1/1997 | Sahay et al. ............... 358/1.14 |
| 5,603,323 A | * 2/1997 | Pflugrath et al. ............ 600/437 |
| 5,655,084 A | * 8/1997 | Pinsky et al. ................... 705/3 |
| 5,675,744 A | * 10/1997 | Tsujii ............................. 705/3 |
| 5,715,496 A | * 2/1998 | Sawada et al. ................. 399/8 |
| 5,715,823 A | * 2/1998 | Wood et al. ................. 600/437 |
| 5,749,907 A | * 5/1998 | Mann ........................... 607/27 |
| 5,790,793 A | * 8/1998 | Higley ....................... 709/218 |
| 5,862,322 A | * 1/1999 | Anglin et al. ................. 714/57 |
| 5,897,498 A | * 4/1999 | Canfield et al. ............ 600/437 |
| 5,964,891 A | * 10/1999 | Caswell et al. ............... 714/31 |
| 5,995,939 A | * 11/1999 | Berman et al. ................. 705/3 |
| 6,032,001 A | * 2/2000 | Miyawaki ...................... 399/8 |

(List continued on next page.)

FOREIGN PATENT DOCUMENTS

| | | | | |
|---|---|---|---|---|
| JP | 11085891 A | * 3/1999 | ........... G06F/19/00 |

OTHER PUBLICATIONS

"Quick Alert from TDI," Sep. 1994, Argus Business, vol. 31 No. 9, p. 84.*

"Motive Software Powers Compaq's Built–In Technician E–Service Tool," Sep. 28, 1999, PR Newswire, p. 4365.*

*Primary Examiner*—Joseph Thomas
*Assistant Examiner*—Carolyn Bleck
(74) *Attorney, Agent, or Firm*—Ostrager Chong Flaherty & Broitman P.C.

(57) ABSTRACT

A central service facility is connected via a network and a uniform service interactive platform to a multiplicity of remotely located diagnostic systems. The diagnostic system is programmed to provide the equipment user with the ability to create an electronic list of non-urgent service tasks to be performed by a field engineer. The task list is transmitted from the diagnostic system to the service center via the network. The service center subsequently transmits the task list to the assigned field engineer via the same network or via any other available communications channel, e.g., a facsimile or wireless communication. Preferably, the task list is provided to the field engineer prior to an on-site visit based upon a call schedule.

10 Claims, 7 Drawing Sheets

U.S. PATENT DOCUMENTS 6,032,184 A * 2/2000 Cogger et al. .............. 709/223
6,092,048 A * 7/2000 Nakaoka ....................... 705/9
6,298,377 B1 * 10/2001 Hartikainen et al. ........ 709/223
6,304,788 B1 * 10/2001 Eady et al. ................... 700/86
6,317,570 B1 * 11/2001 Uchida et al. ................. 399/8
6,321,203 B1 * 11/2001 Kameda ........................ 705/3
6,353,445 B1 * 3/2002 Babula et al. .............. 345/733
6,415,392 B1 * 7/2002 Suzuki et al. ................. 714/27

* cited by examiner

METHOD AND APPARATUS FOR RETRIEVING SERVICE TASK LISTS FROM REMOTELY LOCATED MEDICAL DIAGNOSTIC SYSTEMS AND INPUTTING SUCH DATA INTO SPECIFIC LOCATIONS ON A TABLE

RELATED PATENT APPLICATION

This application is a continuation-in-part application claiming priority from U.S. patent application Ser. No. 09/199,685 filed on Nov. 25, 1998, which issued as U.S. Pat. No. 6,353,445 on Mar. 5, 2002.

FIELD OF THE INVENTION

The present invention relates generally to the field of medical diagnostic and imaging systems. More particularly, the invention relates to a diagnostic system having a user interface which facilitates maintenance, repair and upgrading of the diagnostic system by a service provider.

BACKGROUND OF THE INVENTION

Medical diagnostic and imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic and imaging systems. These include computed tomography (CT) systems, x-ray systems (including both 2Q conventional and digital or digitized imaging systems), magnetic resonance (MR) systems, positron emission tomography (PET) systems, ultrasound systems, nuclear medicine systems, etc. In many instances, these modalities complement one another and offer the physician a range of techniques for imaging particular types of tissue, organs, physiological systems, etc. Health care institutions often arrange several such imaging systems at a single or multiple facilities, permitting its physicians to draw upon such resources as required by particular patient needs.

Modern medical diagnostic systems typically include circuitry for acquiring image data and for transforming the data into a useable form, which is then processed to create a reconstructed image of features of interest within the patient. The image data acquisition and processing circuitry is sometimes referred to as a "scanner" if physical or electronic scanning occurs as part of the imaging process. The particular components of the system and related circuitry, of course, differ greatly between modalities due to their different physics and data processing requirements.

Medical diagnostic systems of the type described above are often called upon to produce reliable and understandable images within demanding schedules and over a considerable useful life. To ensure proper operation, the systems are serviced regularly by highly trained personnel who address imaging problems, configure and calibrate the systems, and perform periodic system checks and software updates. Moreover, service offerings have been supplemented in recent years by service centers capable of contacting scanners at subscribing institutions directly without the need for intervention on the part of the institution personnel. Such centralized servicing is intended to maintain the diagnostic systems in good operational order without necessitating the attention of physicians or radiologists, and is often quite transparent to the institution.

In certain centralized servicing systems, a computerized service center may contact a scanner via a network to check system configurations and operational states, to collect data for report generation, and to perform other useful service functions. Such contacts can be made periodically, such as during system "sweeps", in which a variety of system performance data is collected and stored with historical data for the particular scanner. The data can then be used to evaluate system performance, propose or schedule visits by service personnel, and the like.

While such service techniques have proven extremely valuable in maintaining diagnostic systems, further improvements are still needed. For example, in conventional service systems, contact between the scanners and a centralized service center most often originates with the service center. The scanners are provided with only limited functionality in the ability to identify and define service needs. Even where the scanners have permitted some limited ability to contact networked service providers, intermittent conditions indicative of a potentially serviceable problem may cease by the time the service provider is contacted or recontacts the scanner after a service call. Moreover, although the transparency of interactions between scanners and service centers avoids distracting medical personnel with service updates unnecessarily, some degree of interaction between service centers and institutions is highly desirable. In particular, an interactive service system facilitates valuable exchanges of information, including reports of system performance, feedback on particular incidents requiring attention, updates of system licenses, software, imaging protocols, etc. Currently available service systems permit such interactive exchanges. In particular, a platform has been developed that serves as a base for the interactive servicing needs of different modalities. This platform allows a central service center to exchange information on possible service problems with remotely located scanners, and to retrieve information or data log files from scanners for the purpose of servicing those scanners. One known platform provides a uniform interface permitting clinicians and radiologists to operate a variety of scanners in different modalities, and to report service issues for the scanners, via a uniform, intuitive format.

The known integrated user-interactive platform for servicing diagnostic equipment at remote locations may be configured in software, hardware, or firmware at the scanner or may be installed in a central operator's station linking several scanners in a medical facility. The user interface permits service requests to be generated prior to, during or subsequent to examinations executed on the diagnostic equipment. The user interface also permits service messaging, report generation and retrieval, etc. The user interface is preferably configured as a network browser, which also facilitates linking the scanner or the central facility control station to a network such as an intranet or internet. The same user interface may be integrated into scanners of different modalities, thereby further facilitating service requests and the like by operations personnel, without requiring the personnel to become reacquainted with diverse interfaces in a facility.

While the existing user-interactive platform provides the system user with the capability to send a service request to a service center for immediate assistance, the existing platform does not provide the ability for the end-user of diagnostic equipment to create an electronic worklist of nonemergency items the end-user would like a field engineer to address during the next scheduled on-site visit.

SUMMARY OF THE INVENTION

The present invention relates to medical diagnostic equipment which provides the equipment user with a facility for creating an electronic list of tasks (hereinafter "task list") to be performed by a field engineer which do not require an emergency service call. In accordance with the preferred embodiment of the invention, this electronic task list resides in the medical diagnostic equipment (e.g., a scanner) and is created by the end-user interacting with a graphical user interface. In particular, the task list is created by the user interacting with a so-called "Task List" web page. At a minimum, the task list web page comprises fields for entry of task items. Preferably, the web page also has means for saving or deleting task items listed on the web page.

In accordance with the preferred embodiments of the invention, the task list is transmitted from the diagnostic system to a service center via a network. In accordance with one preferred embodiment, the task list is transmitted concurrently to the assigned field service engineer. In accordance with another preferred embodiment, the service center receives the task list and later transmits it to the assigned field service engineer, via the same network or via any other available communications channel, e.g., a facsimile or wireless communication. The transmission of the electronic task list from the remotely located diagnostic system to the service center may be actuated by either the end-user or the scanner may be programmed to automatically send the task list to the service center in accordance with a schedule. Alternatively, the scanner may be programmed to automatically send the task list in response to a request from the service center. Such requests may be issued to all remote systems by the service center in accordance with a regular schedule or in dependence on when the next service call is scheduled. Optionally, the service center may send a request for transmission of the task list in response to a request from a remotely located field service engineer or prior to a systemically scheduled (such as preventive maintenance) field engineer visit to the remote site. Upon receipt, the task list would be relayed to the field engineer.

Preferably, the task list is automatically "pushed" to the service center by the scanner without the need for system user intervention. Alternatively, the end-user can actuate transmission of the task list to the service center. To facilitate downloading of the task list by the end-user at the scanner, the graphical user interface of the diagnostic system may comprise a virtual "Send" button which is displayed on a task list web page. In response to the end-user clicking on the virtual "Send" button, the scanner would transmit the current task list to the service center via the network. If the network address of the assigned field service engineer is known to the remote system user or is pre-stored in the remote system, then the assigned field service engineer can be copied on any task list transmission to the service center.

Upon receipt of the task list, the service center stores the task list in memory in association with a code identifying the diagnostic system which was the source of the task list. In cases where concurrent transmission to the field service engineer does not occur, the service center automatically relays the task list and the identity of its source system to the assigned field engineer at a remote location via the network (or some other communications channel). In response to transmission of the task list to the field engineer, the service center also transmits a message to the source diagnostic system acknowledging that the task list was sent to the field engineer.

Preferably, the field engineer has a laptop computer with e-mail capability, which can be connected to the network for communicating with the service center. In response to receipt of the task list and source identity from the service center, a pop-up message window notifying the field engineer that a new task list has been received would appear on the laptop display monitor. In response to this message, the field engineer opens up his e-mail to reveal the task list and associated source identifier received from the service center.

In accordance with an alternative preferred embodiment, the service center periodically interrogates the remotely located diagnostic system via the network in accordance with a call schedule. In response to interrogation from the service center, the diagnostic system automatically transmits the service task list to the service center via the network. This procedure is preferably transparent to the end-user, i.e., the web server at the diagnostic system responds to the interrogation without any notice being taken by the end-user. Alternatively, in response to the interrogation from the service center, the web server may produce a pop-up message window on the display monitor of the diagnostic system, which window requests the end-user to transmit the task list to the service center. In response to this message, the user opens up the task list web page and actuates transmission of the task list to the service center, e.g., via the aforementioned virtual "Send" button on the display screen. Again the service center stores the task list in memory in association with a code identifying the diagnostic system which was the source of the task list. The service center then relays the task list and the identity of the source of the task list to the assigned field engineer at the appropriate time, e.g., in accordance with a schedule or in response to log-in of the assigned field engineer.

Preferably, the task list is provided to the field engineer prior to an on-site visit based upon a call schedule. By reviewing the task list prior to the on-site visit, the field engineer can anticipate issues that will need to be resolved and make appropriate preparations for his visit, including packing supplies, replacement parts, equipment, tools or reference materials which may be needed. This system will improve call efficiency and reduce the need for repeat visits.

DETAILED DESCRIPTION OF THE PREFERRED EMBODIMENTS

Figure 1:
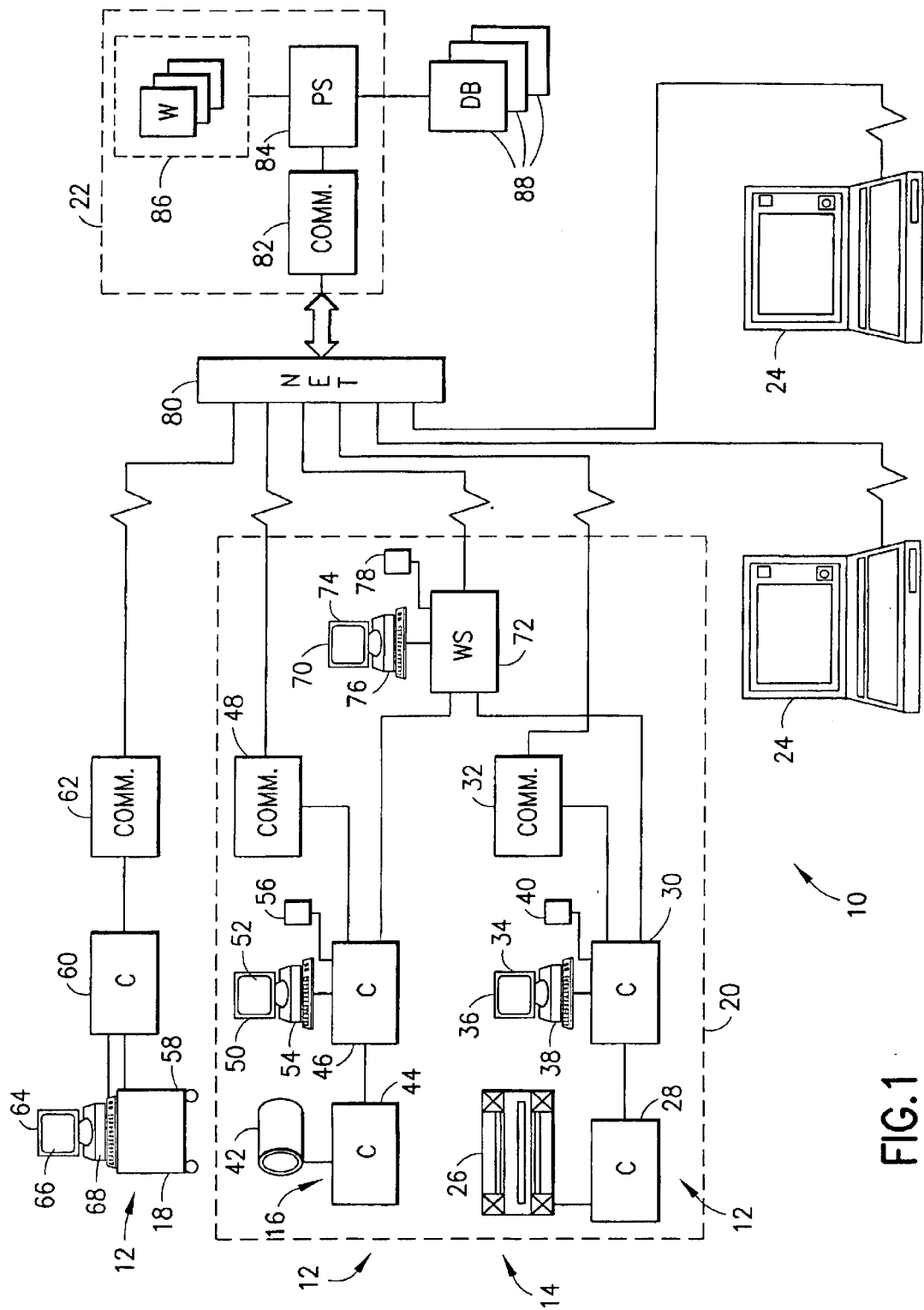
FIG. 1 is a diagrammatical representation of a series of medical diagnostic systems coupled to a service facility via a network connection for providing centralized service and data interchange between the diagnostic systems and the service facility.

Referring to FIG. 1, a service system 10 is illustrated for providing centralized service to a plurality of remotely located medical diagnostic systems 12. In the embodiment shown in FIG. 1, the medical diagnostic systems include a magnetic resonance imaging (MRI) system 14, a computed tomography (CT) system 16, and an ultrasound imaging system 18. The diagnostic systems may be positioned in a single location or facility, such as a medical facility 20, or may be remote from one another as shown in the case of ultrasound system 18. The diagnostic systems are serviced from a centralized service facility 22. Moreover, a plurality of field service units 24 may be coupled in the service system for transmitting service requests, verifying service status, transmitting service data etc. as described more fully below.

In the system shown in FIG. 1, several different system modalities are provided with central service by the service facility. These and other modalities may be similarly serviced by the service facility, depending upon the capabilities of the service facility, the types of diagnostic systems subscribing to service contracts with the facility, as well as other factors. In general, however, the system shown in FIG. 1 is well suited to providing central service to a wide variety of medical diagnostic system modalities, including MRI systems, CT systems, ultrasound systems, positron emission tomography (PET) systems, nuclear medicine systems, etc. Moreover, the various modality systems serviced may be of different type, manufacture and model. Service requests and data transmitted between the diagnostic systems and the service facility include data for identifying the type and modality of the serviced system, as well as data specifically adapted to the system modality and model. It should also be noted that, as used herein, the term "service request" is intended to include a wide range of inquiries, comments, suggestions and other queries or messages generated by a diagnostic system or an institution in which a system is disposed or managed. In particular, such requests may relate to problems occurring on systems, applications questions, questions of a general nature, questions relating to financial or subscription arrangements, information sharing, reports, applications, protocols, etc.

Depending upon the modality of the systems, various subcomponents or subsystems will be included. In the case of MRI system 14, such systems will generally include a scanner 26 for generating pulsed magnetic fields and for collecting signals from emissions by gyromagnetic material within a subject of interest. The scanner is coupled to a control and signal detection circuit 28 which, in turn, is coupled to a system controller 30. System controller 30 includes a uniform platform for interactively exchanging service requests, messages and data with service facility 22 as described more fully below. System controller 30 is linked to a communications module 32, which may be included in a single or separate physical package from system controller 30. System controller 30 is also linked to an operator station 34, which will typically include a computer monitor 36, a keyboard 38, as well as other input devices 40, such as a mouse. In a typical system, additional components may be included in system 14, such as a printer or photographic system for producing reconstructed images based upon data collected from scanner 14. Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics. More particularly, equipment incorporating the service interface disclosed herein may include imaging systems, clinical diagnostic systems, physiological monitoring systems, etc.

Similarly, CT system 16 will typically include a scanner 42 which detects portions of x-ray radiation directed through a subject of interest. Scanner 42 is coupled to a generator and controller, as well as to a signal acquisition unit, represented collectively at reference numeral 44, for controlling operation of an x-ray source and gantry within scanner 42, and for receiving signals produced by a detector array moveable within the scanner. The circuitry within the controller and signal acquisition components is coupled to a system controller 46 which, like controller 30 mentioned above, includes circuitry for commanding operation of the scanner and for processing and reconstructing image data based upon the acquired signals. System controller 46 is linked to a communications module 48, generally similar to communications module 32 of MRI system 14, for transmitting and receiving data for central service of system 16. Also, system controller 46 is coupled to an operator station 50 which includes a computer monitor 52, a keyboard 54, as well as other input devices 56, such as a mouse. Moreover, like MRI system 14, CT system 16 will generally include a printer or similar device for outputting reconstructed images based upon data collected by scanner 42.

Other modality devices will include circuitry and hardware particularly configured for acquiring or producing signals in accordance with their particular design. In particular, in the case of ultrasound system 18, such systems will generally include a scanner and data processing unit 58 for transmitting ultrasound signals into a subject of interest, and for acquiring resultant signals which are processed for reconstructing a useful image. The system includes a system controller 60 which regulates operation of scanner 58 and which processes acquired signals to reconstruct the image. Moreover, system 18 includes a communications module 62 for transmitting service requests, messages and data between system controller 60 and service facility 22. System 18 also includes an operator station 64, including a monitor 66, as well as input devices such as a keyboard 68.

Where more than one medical diagnostic system is provided in a single facility or location, as indicated in the case of MRI and CT systems 14 and 16 in FIG. 1, these may be coupled to a management station 70, such as in a radiology department of a hospital or clinic. The management station may be linked directly to controllers for the various diagnostic systems, such as controllers 30 and 46 in the illustrated example. The management system may include a computer workstation or personal computer 72 coupled to the system controllers in an intranet configuration, a file-sharing configuration, a client/server arrangement, or any other suitable arrangement. Management station 70 will typically include a monitor 74 for viewing system operational parameters, analyzing system utilization, and exchanging service requests and data between the remote facility 20 and the central service facility 22. Input devices, such as a standard computer keyboard 76 and mouse 78, may also be provided to facilitate the user interface. It should be noted that, alternatively, the management system, or other diagnostic system components, may be stand-alone, i.e., not coupled directly to a diagnostic system. In such cases, the service platform described herein, and some or all of the service functionality may nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 72 and field service units 24, may be linked to service facility 22 via a remote access network 80. For this purpose, any suitable network connection may be employed. Preferred network configurations include both proprietary or dedicated networks, as well as open networks, such as the Internet. Data may be exchanged between the diagnostic systems, field service units 24, and central service facility 22 in any suitable format, such as in accordance with the Internet Protocol (IP), the Transmission Control Protocol (TCP), or other known protocols. Moreover, certain of the data may be transmitted or formatted via markup languages, such as the HyperText Markup Language (HTML), or other standard languages. The preferred interface structures and communications components are described in greater detail below.

Within service facility 22, messages, service requests and data are received by communication components as indicated generally at reference numeral 82. Components 82 transmit the service data to a service center processing system, represented generally at reference numeral 84 in FIG. 1. The processing system manages the receipt, handling and transmission of service data to and from the service facility. In general, processing system 84 may include one or a plurality of computers, as well as dedicated hardware or software servers for processing the various service requests and for receiving and transmitting the service data, as described more fully below. Service facility 22 also includes a bank of operator workstations 86, which may be staffed by service engineers who address the service requests and provide off- and on-line service to the diagnostic systems in response to the service requests. Also, processing system 84 may be linked to a system of databases or other processing systems 88 at or remote from the service facility 22. Such databases and processing systems may include extensive database information on operating parameters, service histories, etc., both for particular subscribing scanners and for extended populations of diagnostic equipment. As described below, such databases may be employed both for servicing of particular diagnostic systems and for tracking such servicing, as well as for deriving comparison data for use in servicing a particular system or a family of systems.

Figure 2:
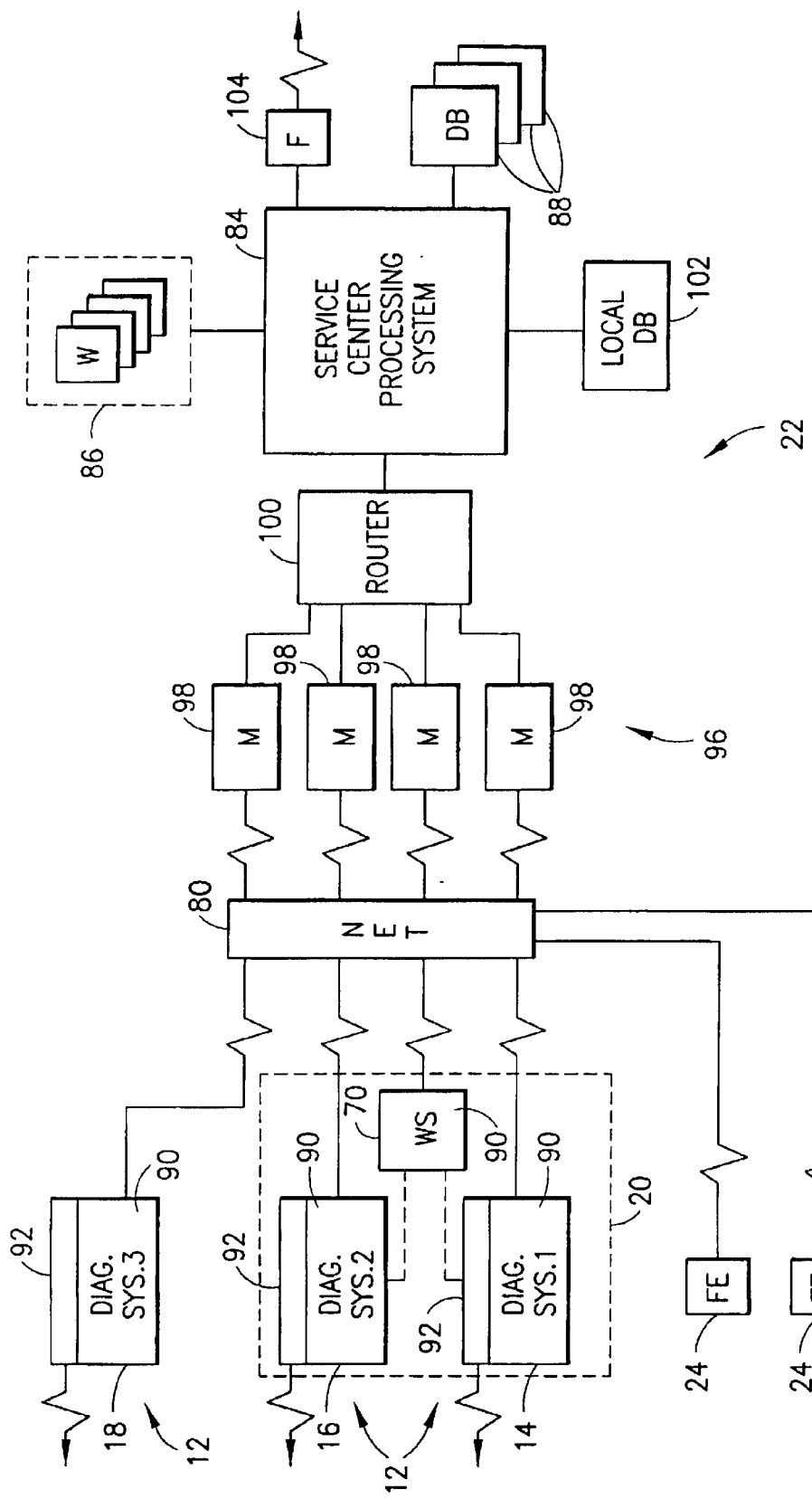
FIG. 2 is a block diagram of the systems shown in FIG. 1, illustrating certain functional components of the diagnostic systems and the service facility.

FIG. 2 is a block diagram illustrating the foregoing system components in a functional view. As shown in FIG. 2, remotely located field service units 24 and diagnostic systems 12 can be linked to the central service facility 22 via a network connection as illustrated generally at reference numeral 80. Within each diagnostic system 12, a uniform service platform 90 is provided. Platform 90, which is described in greater detail below with particular reference to FIG. 3, includes hardware, firmware, and software components adapted for composing and transmitting service requests and service task lists, transmitting and receiving service data, establishing network connections, and managing financial or subscriber arrangements between the diagnostic system and the service facility. Preferably, the platform 90 is integrated into the system controller of the diagnostic system. These platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 70 is provided, a similar uniform platform is preferably loaded on the management station to facilitate direct interfacing between the management station and the service facility. In addition to the uniform service platform 90, each diagnostic system is preferably provided with an alternative communications module 92, such as a facsimile transmission module for sending and receiving facsimile messages between the remotely located scanner and the central service facility.

Messages and data transmitted between the diagnostic systems and the service facility traverse a security barrier or "firewall" contained within processing system 84, which prevents unauthorized access to the service facility in a manner generally known in the art. A modem rack 96, including a series of modems 98, receives the incoming data, and transmits outgoing data through a router 100, which manages data traffic between the modems and the service center processing system 84.

As mentioned above, processing system 84 receives and processes the service requests and data, and interfaces with additional service components, both at the service facility and remote from the facility. As shown in FIG. 2, operator workstations 86 are coupled to the processing system, as are remote databases or computers 88. In addition, at least one local service database 102 is provided for verifying license and contract arrangements, storing service record files, log files, etc. Moreover, one or more communication modules 104 are linked to processing system 84 to send and receive facsimile transmissions between the service facility and the diagnostic systems or field service units.

Figure 3:
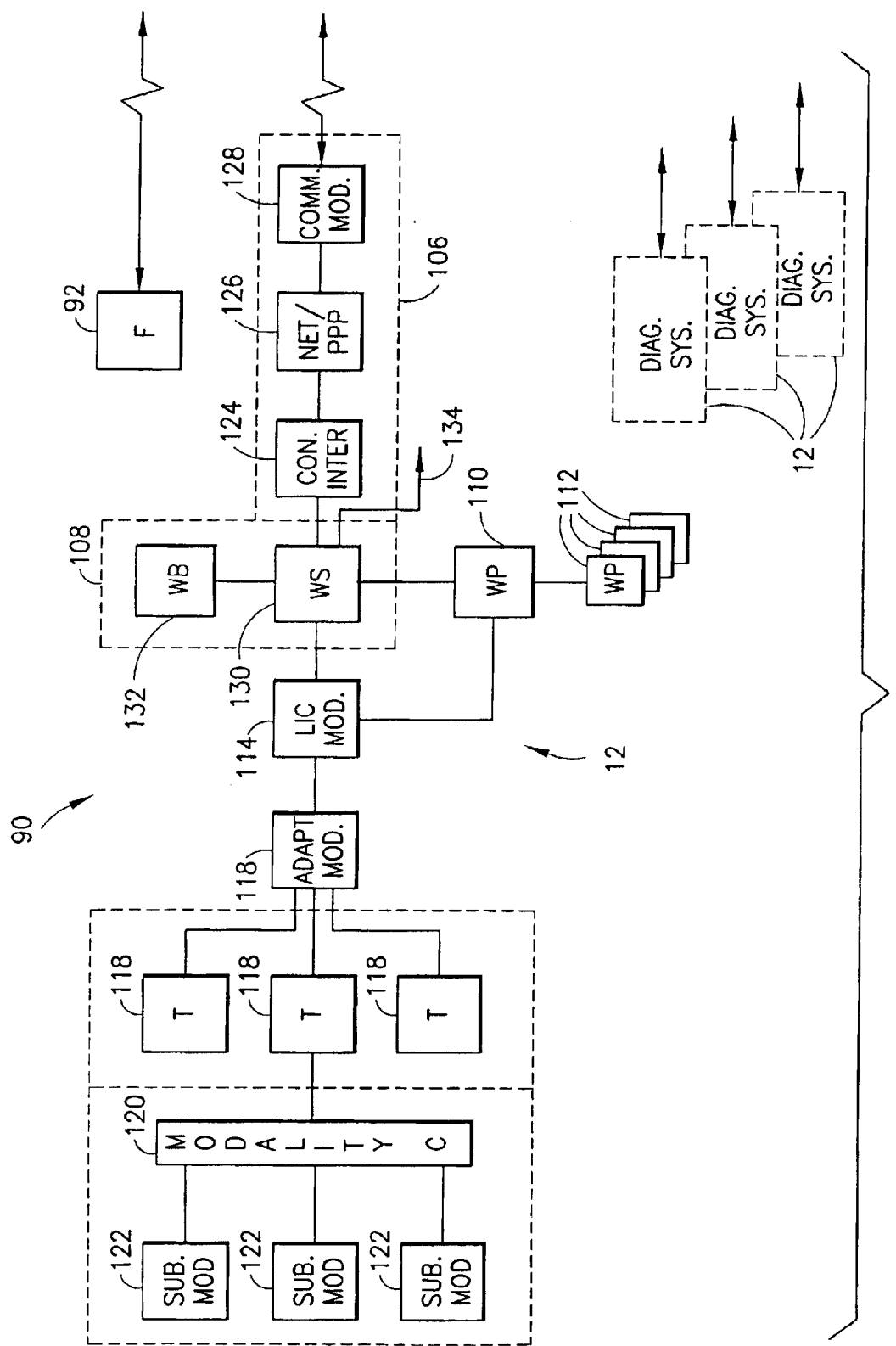
FIG. 3 is a block diagram of certain functional components within a diagnostic system of the type shown in FIGS. 1 and 2 for facilitating interactive centralized is servicing of the diagnostic system.

FIG. 3 shows the various functional components comprising the uniform service platform 90 within each diagnostic system 12. The uniform platform includes a device connectivity module 106, as well as a web services connectivity module 108. Web services connectivity module 108 accesses a main web page 110 which, as mentioned above, is preferably a markup language page, such as an HTML page displayed for the system user on a monitor at the diagnostic system. Main web page 110 is preferably accessible from a scanner console interface in which the user will configure examination requests, view the results of examinations, etc., such as via an on-screen icon. Through main web page 110, a series of additional web pages 112 are accessible. Such web pages permit service requests and service task lists to be composed and transmitted to the central service facility, and facilitate the exchange of other messages, reports, software, protocols, etc. as described more fully below. It should be noted that as used herein, the term "page" includes a user interface screen or similar arrangement which can be viewed by a user of the diagnostic system, such as screens providing graphical or textual representations of data, messages, reports, etc. Moreover, such pages may be defined by a markup language or a programming language such as Java, perl, java script, or any other suitable language.

Web services connectivity module 108 is coupled to a license module 114 for verifying the status of the license, fee or contractual subscriptions between the diagnostic system and the service facility. As used herein, the term "subscription" should be understood to include various arrangements, contractual, commercial or otherwise for the provision of services, information, software, and the like, with or without payment of a fee. Moreover, the particular arrangements managed by systems as described below may include several different types of subscriptions, including time-expiring arrangements, one-time fee arrangements, and so-called "pay per use" arrangements, to mention but a few.

License module 114 is, in turn, coupled to one or more adapter utilities 116 for interfacing the browser, server, and communications components with modality interface tools 118. In a preferred configuration, several such interface tools are provided for exchanging data between the system scanner and the service platform. For example, modality interface tools 118 may include applets or servlets for building modality-specific applications, as well as configuration templates, graphical user interface customization code, etc. Adapters 116 may interact with such components, or directly with a modality controller 120 which is coupled to modality-specific subcomponents 122. The modality controller 120 and modality-specific subcomponents 122, will typically include a preconfigured processor or computer for executing examinations, and memory circuitry for storing image data files, log files, error files, etc. Adapter 116 may interface with such circuitry to convert the stored data to and from desired protocols, such as between the HyperText Transfer Protocol (HTTP) and DICOM, a standard for digital imaging communications. Moreover, transfer of files and data may be performed via any suitable protocol, such as a file transfer protocol (FTP) or other network protocol.

In the illustrated embodiment, device connectivity module 106 includes several components for providing data exchange between the diagnostic system and the central service facility. In particular, a connectivity service module 124 provides for interfacing with web services connectivity module 108. A Point-to-Point Protocol (PPP) module 126 is also provided for transmitting Internet Protocol (IP) packets over remote communication connections. Finally, a modem 128 is provided for receiving and transmitting data between the diagnostic system and the central service facility. As will be appreciated by those skilled in the art, various other network protocols' and components may be employed within device connectivity module 106 for facilitating such data exchange.

Web services connectivity module 108 preferably includes a server 130 and a browser 132. Server 130 facilitates data exchange between the diagnostic system and the service facility, and permits a series of web pages 110 and 112 to be viewed via browser 132. In a preferred embodiment, server 130 and browser 132 support HTTP applications and the browser supports Java applications. Other servers and browsers or similar software packages may, of course, be employed for exchanging data, service requests, messages, and software between the diagnostic system and the central service facility. Finally, a direct network connection 134 may be provided between web server 130 and a local area network (not shown) within the medical facility.

In a preferred embodiment, the components comprising web services connectivity module may be configured via an application stored as part of the uniform platform. In particular, a Java application licensed to a service engineer enables the engineer to configure the device connectivity at the diagnostic system to permit it to connect with the central service facility. Features of the application are segmented into separate tabbed pages accessible by the service engineer. The application is entered via a license agreement screen. Once accepted, the service engineer can configure parameters of the system modem, the schedule for running automatic diagnostic checks, and establish electronic messaging, such as for automatic service report generation. Once the modem is configured, the service engineer establishes contact with the service facility and provides data enabling the service facility to download any remaining data needed for secure communication between the diagnostic system and the service center. Upon exit from the application, a configuration status is presented to the service engineer, including status of an automatic test of connectivity between the sites.

Figure 4:
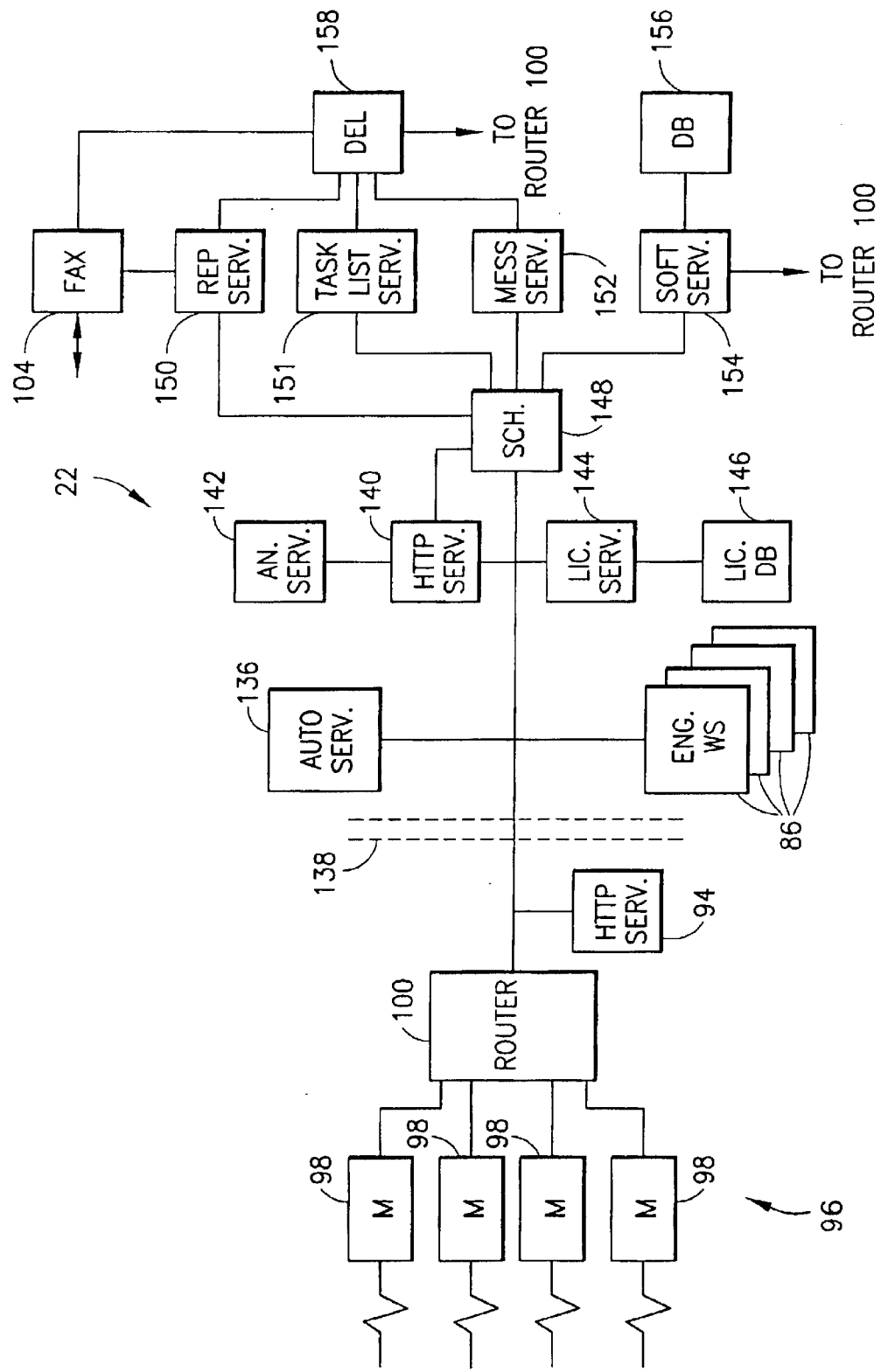
FIG. 4 is a block diagram of certain of the functional components of the service facility in accordance with the preferred embodiment of the invention for rendering interactive centralized service to a plurality of remotely located medical diagnostic systems.

FIG. 4 illustrates exemplary functional components for service facility 22. As indicated above, service facility 22 includes a modem rack 96 comprising a plurality of modems 98 coupled to a router 100 for coordinating data communications with the service facility. A so-called "front office" HTTP service server 94 receives and directs incoming and outgoing transactions with the facility. Server 94 is coupled to the other components of the facility through a firewall 138 for system security. Operator workstations 86 are coupled to the port manager for handling service requests and transmitting messages and reports in response to such requests. An automated service unit 136 may also be included in the service facility for automatically responding to certain service requests, sweeping subscribing diagnostic systems for operational parameter data, etc. In a preferred embodiment, the automated service unit 136 may operate independently of or in conjunction with the interactive service components comprising processing system 84. It should be noted that other network or communications schemes may be provided for enabling the service facility to communicate and exchange data and messages with diagnostic systems and central service units, such as systems including outside Internet service providers and virtual private networks.

Behind firewall 138, a so-called "back office" HTTP application server 140 coordinates handling of service requests, messaging, reporting, software transfers, etc. Other servers may be coupled to HTTP server 140, such as service analysis servers 142 configured to address specific types of service requests. In the illustrated embodiment, processing system 84 also includes a license server 144 which is coupled to a license database 146 for storing, updating and verifying the status of diagnostic system service subscriptions. Alternatively, license server 144 may be placed outside of firewall 138 to verify subscription status prior to admission to the service facility.

Handling of service requests, service task lists, messaging, and reporting is further coordinated by a scheduler module 148 coupled to HTTP server 140. Scheduler module 148 coordinates activities of other servers comprising the processing system, such as a report server 150, a task list server 151, a message server 152, and a software download server 154. As will be appreciated by those skilled in the art, servers 150, 151, 152 and 154 are coupled to memory devices (not shown) for storing data such as task lists, addresses, log files, message and report files, applications software, etc. In particular, as illustrated in FIG. 4, software server 154 is coupled via one or more data channels to a storage device 156 for containing transmittable software packages which may be sent directly to the diagnostic systems, accessed by the diagnostic systems, or supplied on pay-per-use or purchase basis. Task list, message and report servers 151, 152 and 154 are further coupled, along with communications module 104, to a delivery handling module 158, which is configured to receive outgoing messages, ensure proper connectivity with diagnostic systems, and coordinate transmission of messages to the diagnostic systems and the transmission of messages and task lists to remotely located field engineers via the network.

Figure 5:
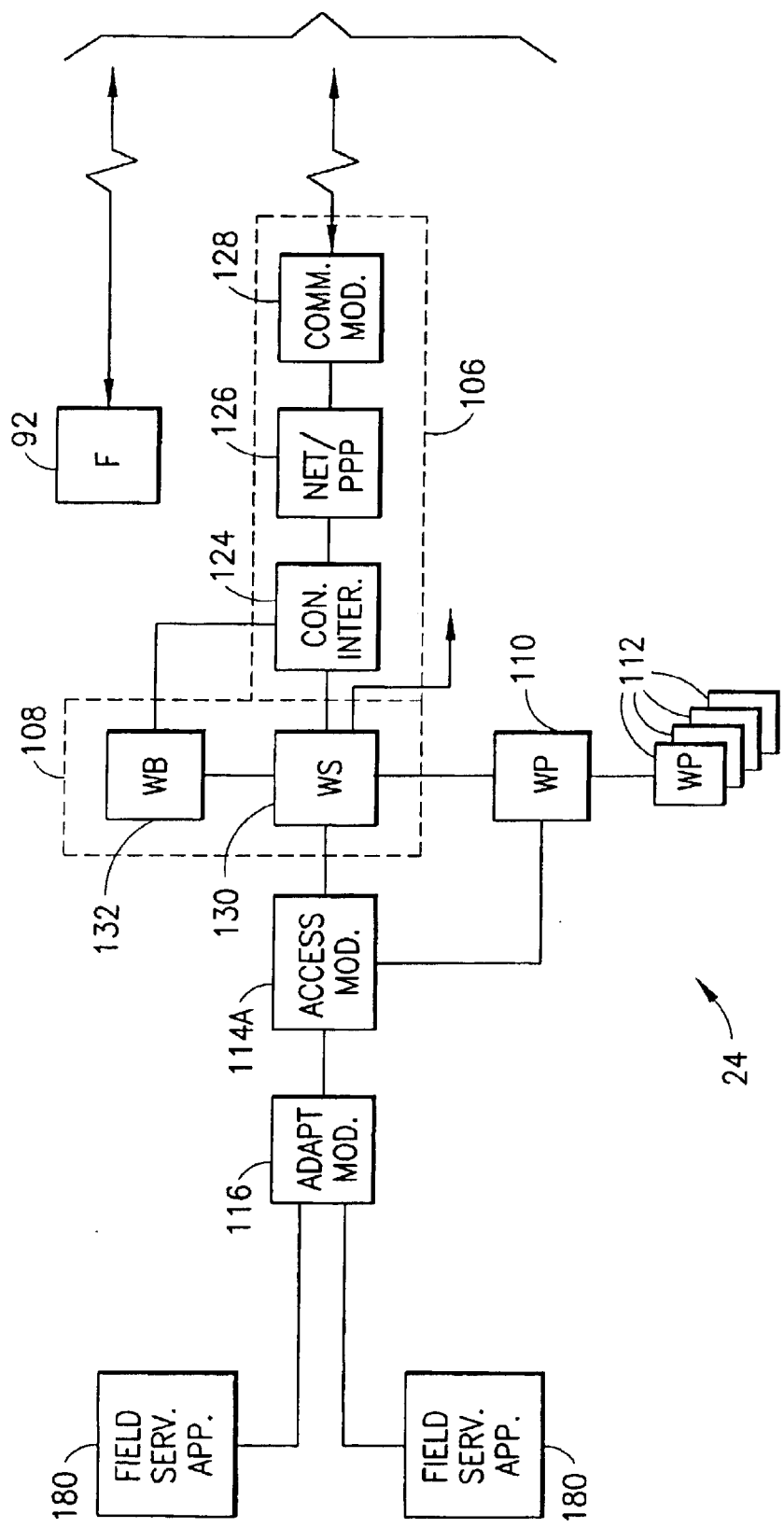
FIG. 5 is a block diagram of functional components within a field service unit which can be coupled to the diagnostic systems and to the service facility for exchanging service information with a field service engineer.

FIG. 5 shows functional components contained within an exemplary field service unit 24. Field service unit 24 may include a portable computer designed for use by remote service engineers. The unit includes a service platform which, in turn, includes certain functional circuitry for establishing a uniform service base as discussed above for the diagnostic systems themselves. Moreover, the service units include specific service tools which enable the field engineer to request and receive messages, task lists from specific diagnostic systems, reports on specific diagnostic systems, service schedules, etc. from the service center. Through the service platform, the field engineer may access system configurations, historic log information, system network information, analysis logs and data, etc. The field engineer may also update service records either from the field service unit or from the diagnostic system, as desired.

Thus, as shown in FIG. 5, an exemplary field service unit includes a device connectivity module 106 and a web services connectivity module 108. Device connectivity module 106 may include connectivity interface circuitry 124, a network or PPP module 126, and a modem 128, as described above for the diagnostic system with reference to FIG. 3. The web services connectivity module 108 may, in turn, include a server 130 and browser 132 substantially identical to those of the diagnostic systems, enabling the field engineer to receive, view and compose messages, reports, etc. via a main web page 110 and a series of web pages 112. Moreover, an access module 114A is provided for allowing the service facility to verify the license and security status of the field service unit. For example, the access module, in cooperation with circuitry at the service facility, may permit a field service engineer to access data or applications providing some or all of the functionality offered to service engineers at the service facility. Such functions may be similar to those provided at the diagnostic systems themselves, or may offer the service engineer a wider range of service options. One or more adapter modules 116 provide for interfacing the network circuitry with various field service tools. In particular, the field service unit may be equipped with service applications, as indicated at blocks 180, such as for analyzing diagnostic system performance data, scheduling regular or special service calls, scheduling for shipment of replacement parts, etc. Other service applications may include applications generally similar to those executed on the operator workstations 86 of the service facility (see FIG. 4). Such applications may permit the field service engineer to address service requests at the diagnostic system site or remote from the site, as required, and transmit service messages and updates via the remote field service unit.

In a preferred embodiment, the foregoing functional circuitry may be configured as hardware, firmware, or software on any appropriate computer platform. For example, the functional circuitry of the diagnostic systems may be programmed as appropriate code in a personal computer or workstation, either incorporated entirely in or added to the system scanner. The functional circuitry of the service facility may include additional personal computers or workstations, in addition to a main frame computer in which one or more of the servers, the scheduler, etc., are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of service data between the diagnostic systems and a central service facility, which is preferably implemented in an interactive manner to provide regular updates to the diagnostic systems of service activities.

Figure 6:
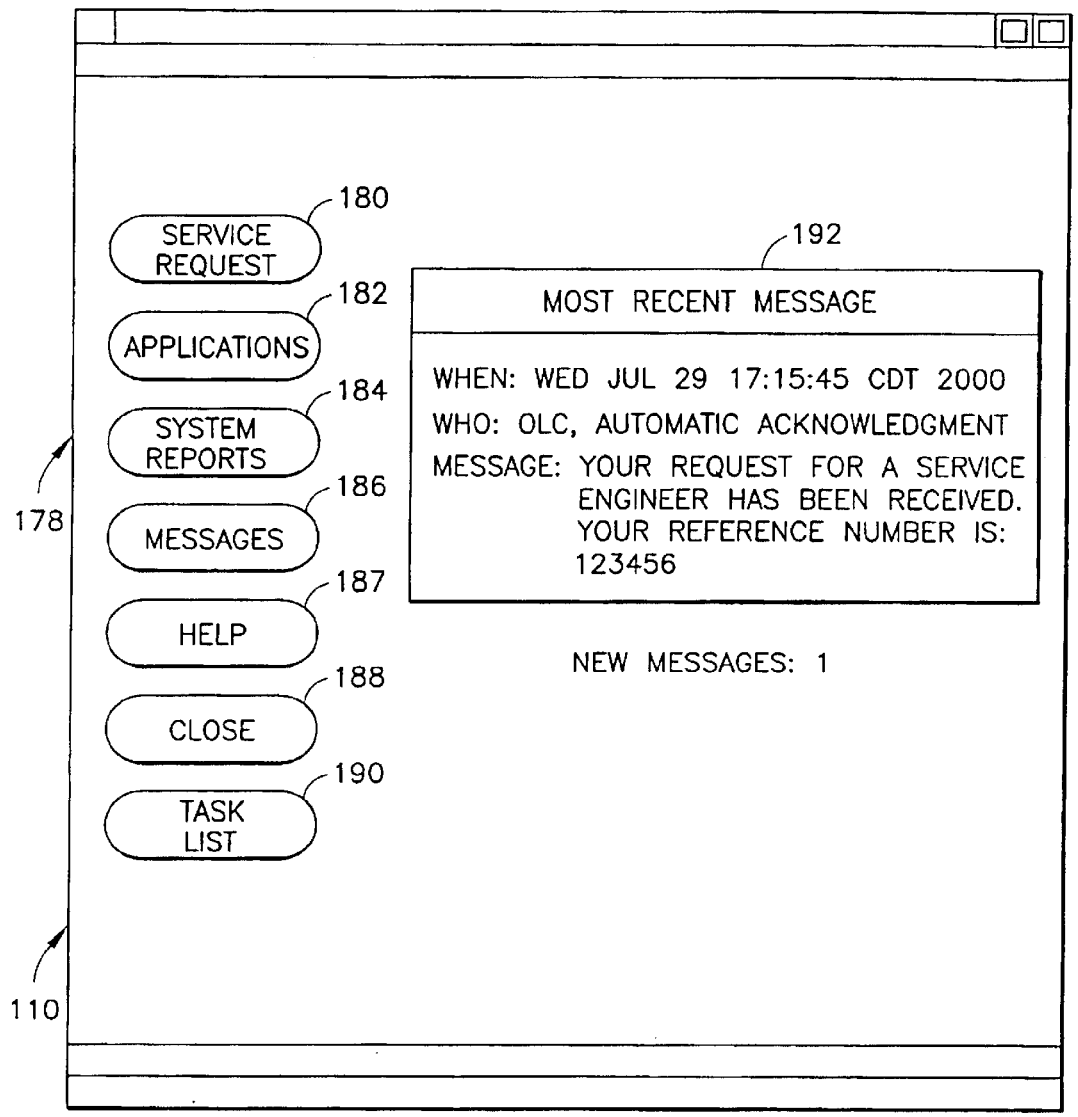
FIG. 6 is an exemplary user interface page incorporated in the diagnostic system for placing service requests, and sending and receiving service data between the diagnostic system and a central service facility.

As described above, both the diagnostic systems and the field service units preferably facilitate interfacing between a variety of diagnostic system modalities and the central service facility via a series of interactive user-viewable pages. FIG. 6 illustrates an exemplary main web page which presents the main menu for selecting a desired interactive mode, e.g., composing service requests and task lists, selecting and transferring messages, reports and diagnostic system software, etc. It should be noted that through the following discussion, reference is made to viewable pages for interfacing in the language of the present description. However, in a preferred embodiment, the platform may be configured to present such interface pages in several different languages, depending upon the country in which the system is installed.

As illustrated first in FIG. 6, a main web page 110 is accessible from a normal diagnostic system screen viewable on a diagnostic system monitor (e.g., monitors 36, 52 or 66). The main web page 110 may therefore be viewable by clicking an input device such as a mouse on an icon (not shown) on the normal operational screen. Main web page 110 includes a series of navigation devices 178 in the form of graphical (i.e., virtual) buttons for accessing other interface pages in the graphical user interface. In the illustrated embodiment, these graphical devices include a service request button 180 for accessing a service request page, an applications button 182 for accessing an applications page, a system reports button 184 for accessing service reports, a messages button 186 for sending and receiving interactive service messages, and a task list button 190 for accessing a task list page. A help button 187 is provided for accessing user information, help topics etc., which may be resident on the system; or available through on-line sources viewable through the system browser. A close or exit button 188 is provided for returning to the normal scanner interface page. In addition to these navigational devices, main page 110 includes a message area 192 in which information regarding the most recent messages is displayed. This information may include identification of the time and date received, the originator of the message, and a brief summary of the message content or title. Thus, upon accessing main page 110, the system user is made aware of service activities carried out by the central service facility or field service engineer.

Figure 7:
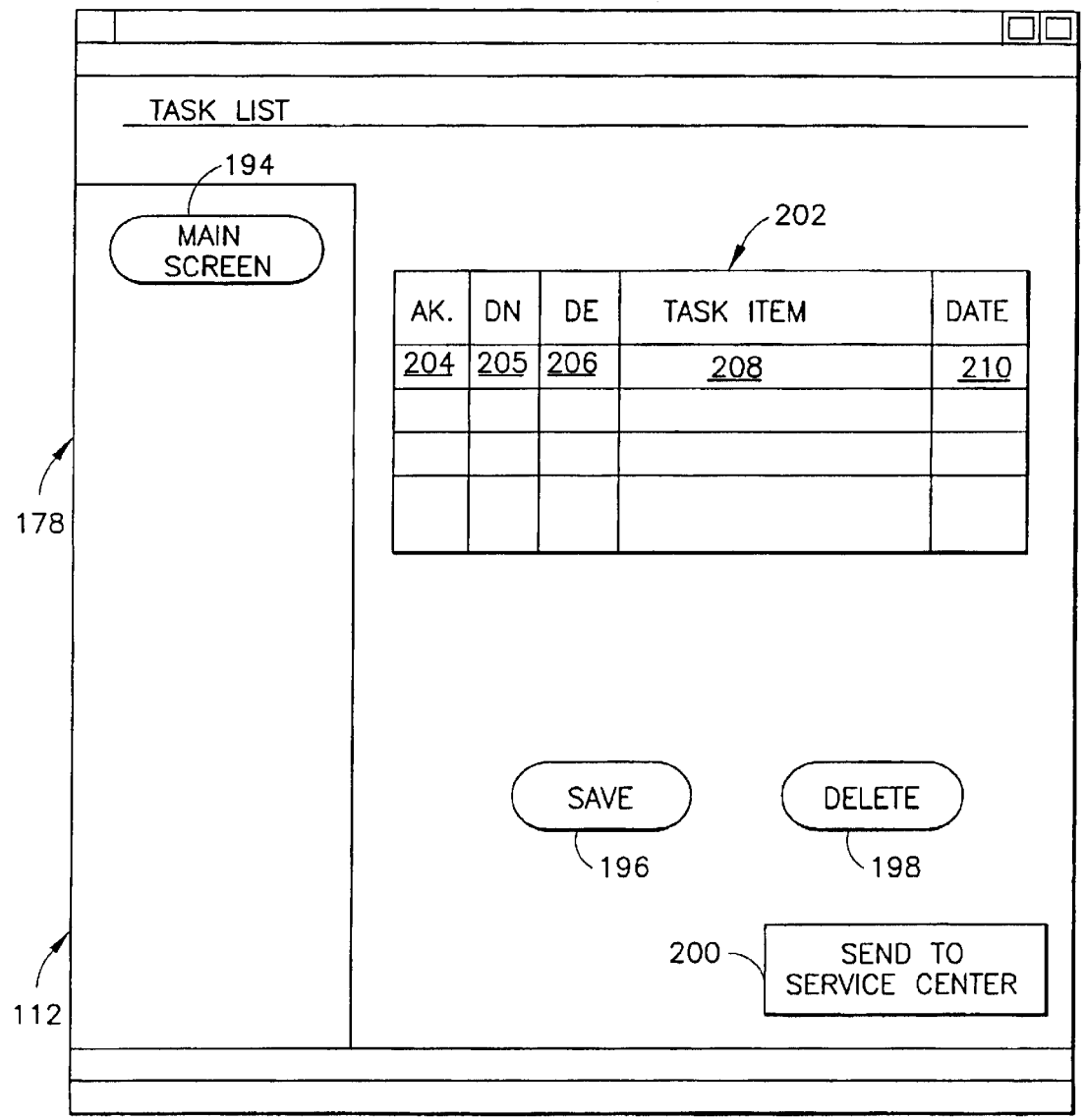
FIG. 7 is a second user interface page for conveying a field engineer task list from the scanner operator to the service facility in accordance with the preferred embodiment of the invention.

FIG. 7 illustrates a task list page 112 accessed by actuation of the task list button 190 on the main web page (see FIG. 6). The task list page 112 includes a main menu button 194 for returning to the main web page shown in FIG. 6. As mentioned above, the uniform graphical user interface facilitates formulation of service task lists and enables system designers to permit retrieval of such task lists in a similar manner across several diagnostic system modalities. FIG. 7 illustrates an exemplary interface page for formulating such task lists. In the page shown in FIG. 7, a task list 202 comprising a multiplicity of fields is displayed. The task list is intended to be a list of non-urgent service-related tasks which the end-user wishes the assigned field service engineer to perform on the diagnostic system during his/her next on-site visit and which the central service facility may automatically "pull" from the remotely located system, which the remote system may automatically "push" to the service center, or which the remote system user may transmit to the service center. Each task item is entered by clicking on a field 208 in the Task List column and then entering a description of the task via the operator station keyboard. The date on which the task item was entered can be entered by the end-user in a field 210 in the Date column. Alternatively, the uniform service platform may be programmed to enter the date automatically each time a task item is entered. After the task items have been entered, the task list can be saved in memory in the diagnostic system by clicking on the virtual Save button 196. One or more items can be deleted by clicking on the associated field 206 in the Delete column (abbreviated "DE" in FIG. 7) of the task list, in response to which the uniform service platform displays a check mark or other icon, and then clicking on the virtual Delete button 198. All items checked off will be deleted. Optionally, the end-user can send the task list to the central service facility by clicking on a virtual Send button 200. It should be noted that the server included in the uniform platform already includes unique system identification data which supplements the information input by the user. The unique system identification data is automatically sent to the service center along with the task list. The task list template also includes an Acknowledgment column (abbreviated "AK" in FIG. 7) of fields 204 which are checked off by the uniform service platform in response to receipt of an acknowledgment from the service center that the task list has been forwarded to the field service engineer assigned to that diagnostic system. Subsequent items added to the task list will not have a check mark in the Acknowledgment column until such time as the updated task list is sent to the service center and then forwarded to the field engineer. The task list template further includes a Done column (abbreviated "DN" in FIG. 7) of fields 205 which are checked off by the field engineer when he/she is on site and has completed the associated task items. Later when the end user views the task list web page, the end-user may delete all items which have been performed and checked off by the field engineer in the manner previously described.

Referring back to FIG. 2, the task list and source system identifier are transmitted from the diagnostic system 12 to the service center 22 via the network 80. Optionally, the service center 22 subsequently transmits the task list and the identity of the source system to the field service unit 24 of the field service engineer assigned to the source system via the same network or via any other available communications channel, e.g., a facsimile or wireless communication. The transmission of the electronic task list from the remotely located diagnostic system 12 to the service center 22 may be actuated by either the end-user, the scanner or the service center. Optionally, the service center may actuate task list retrieval in response to a request for task list retrieval received from the field service engineer or prior to a systemically scheduled (such as preventive maintenance) field engineer visit to the remote site.

Referring to FIG. 4, the task list server 151 is programmed with the capability to interrogate any remotely located diagnostic system and retrieve the service task list stored in that system. The task list server 151 sends a message to the particular diagnostic system requesting that system to transmit its service task list to the service center. The message is sent at a time determined by the scheduler 148. The task list server sends the request message via the delivery handling module 158, router 100, a modem 98 and network 80. In response to the request, the web server 130 (see FIG. 3) of the interrogated diagnostic system retrieves its task list from memory and transmits it to the service center, e.g., via the device connectivity module 106 and the network 80. This procedure is preferably transparent to the end-user, i.e., the web server at the diagnostic system responds to the interrogation without any notice being taken by the end-user. Alternatively, in response to the interrogation from the service center, the web server may produce a pop-up message window on the display monitor of the diagnostic system which requests that the end-user transmit the task list to the service center. In response to this message, the user opens up the task list web page shown in FIG. 7 and actuates transmission of the task list to the service center, e.g., via the aforementioned virtual "Send" button 200 on the display screen.

Upon receipt of the task list by the service center processing system 84, the task list is routed to the task list server 151 via the scheduler 148 shown in FIG. 4. The task list is stored in memory in association with the code identifying the diagnostic system which originated the task list. The task list server is programmed to determine which field service engineer is assigned to that diagnostic system. Subsequently, the task list server 151 sends the task list and source system identifier to the field service unit 24 of the assigned field engineer at the appropriate time, e.g., in accordance with a schedule or in response to log-in of the assigned field engineer. Preferably, the task list is provided to the field engineer prior to an on-site visit based upon a call schedule. The task list and source identifier are sent to the field engineer via the delivery handling module 158, router 100, a modem 98 and network 80, preferably in the form of an e-mail transmission.

In response to transmission of the task list to the field engineer, the service center also transmits a message to the source diagnostic system acknowledging that the task list has been sent to the field engineer. In response to that acknowledgment, the web server for that diagnostic system will update the task list file such that check marks will appear in fields 204 corresponding to task items transmitted when the task list web page 112 is displayed.

Preferably, the field service unit 24 is a laptop computer which can be connected to the network 80 for communicating with the service center 22. Preferably the laptop computer is programmed with e-mail capability. In response to receipt of the task list and source identity from the service center, a pop-up message window notifying the field engineer that a new task list has been received appears on the laptop display monitor. In response to this message, the field engineer opens up his e-mail to reveal the task list and associated source identifier received from the service center. By reviewing the task list prior to the on-site visit, the field engineer can anticipate issues that will need to be resolved and make appropriate preparations for his visit, including packing supplies, replacement parts, equipment, tools or reference materials which may be needed. This system will improve call efficiency and reduce the need for repeat visits.

In accordance with a further aspect of the invention, the service facility may sweep a selected set of diagnostic systems for service task lists. As used herein, the term "sweep" refers generally to a process of connecting system components, such as via a network connection, identifying desired data, and transmitting the data, either in an "upload" or a "download" scenario, depending upon the nature of the data and its use in servicing a system. Such sweeps may occur on regularly scheduled bases, at desired times (e.g., at off-peak utilization times) or on demand by a system user or a system application. The task lists may be stored as specific data files in the remote diagnostic systems, which files are accessed either through intervention of a service engineer or automatically by the service facility processing system. Once the task list data is accessed, it is transmitted to and stored in memory at the service facility. Subsequently, the service facility may disconnect from the diagnostic system.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A system comprising a central service facility connected to a multiplicity of remotely located diagnostic systems via a network, wherein each of said diagnostic systems comprises a graphical user interface for inputting an electronic task list comprising at least one item, each item representing a respective-non-urgent service task to be performed on said diagnostic system, and then sending said electronic task list from said diagnostic system to said central service facility via said network, wherein said graphical user interface in each of said multiplicity of diagnostic systems further comprises means for displaying said electronic task list in the form of a table having rows and columns of fields, each of said rows comprising a respective field in a first column and a respective field in a second column, one of said rows comprising a field in said first column containing data that is recognized as being a service task description of a non-urgent service task and a field in said second column containing data that is recognized as being an indicator that the task list has been received from the diagnostic system by the central service facility and forwarded to a field service unit of a responsible field service engineer, wherein each of said diagnostic systems further comprises an input device operated by a diagnostic system user for inputting service task descriptions in said first column of said table, and networking software that automatically inputs said task list received indicators in said second column in response to acknowledgements from said central service facility that the task list has been received and forwarded to said field service unit.

2. The system as recited in claim 1, wherein said central service facility comprises a task list server which is programmed to send a message to said diagnostic system via said network requesting said diagnostic system to perform said sending step.

3. The system as recited in claim 2, wherein said central service facility further comprises a scheduler for actuating said task list server to send said message in accordance with a call schedule stored in memory associated with said scheduler.

4. The system as recited in claim 2, wherein said task list server is further programmed to send said electronic task list to a remotely located field service unit.

5. The system as recited in claim 4, wherein said electronic task list is sent to said field service unit via said network.

6. The system as recited in claim 4, wherein said task list server is further programmed to send a message to said diagnostic system via said network acknowledging that said electronic task list has been sent to said field service unit.

7. The system as recited in claim 1, wherein each of said rows further comprises a respective field in a third column, said field in said third column of said one row containing data that is recognized as being an indicator that the service task described in the associated service task description has been completed.

8. A medical diagnostic system comprising:

means for connecting to a network;

a graphical user interface that displays a web page having an electronic task list in the form of a table having rows and columns of fields, each of said rows comprising a respective field in a first column, one of said rows comprising a field in said first column containing data that is recognized as being a service task description of a non-urgent service task to be performed on said diagnostic system; and a web server programmed for transmitting said electronic task list to said means for connecting to a network in response to a send command input via said graphical user interface, wherein each of said rows further comprises a respective field in a second column, said one row comprising a field in said second column that has been filled by said web server with a visible indicator in response to receipt by said web server of a predetermined message via said means for connecting to a network, said predetermined message representing an acknowledgment from a central service facility that said electronic task list has been sent to a field engineer assigned to said medical diagnostic system.

9. The medical diagnostic system as recited in claim 8, wherein said graphical user interface comprises a user input device, each said rows further comprises a respective field in a third column, said one row comprising a field in said third column containing a visible indicator in response to a predetermined input via said user input device, said predetermined input representing a notice from a field service engineer that the service identified by a corresponding item in said electronic task list has been completed.

10. The medical diagnostic system as recited in claim 8, wherein said graphical user interface comprises a virtual Send button and said web server comprises means for sending said electronic task list to said means for connecting to a network in response to clicking on said virtual Send button.

* * * * *